(12) United States Patent
Peukert et al.

(10) Patent No.: US 8,398,688 B2
(45) Date of Patent: Mar. 19, 2013

(54) BONE SCREW

(75) Inventors: Andrea Peukert, Tuttlingen (DE); Jens Beger, Tuttlingen (DE); Alexander Haas, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 13/166,416

(22) Filed: Jun. 22, 2011

(65) Prior Publication Data

US 2011/0251649 A1    Oct. 13, 2011

Related U.S. Application Data

(63) Continuation of application No. 11/732,752, filed on Apr. 4, 2007, now Pat. No. 7,988,714, which is a continuation of application No. PCT/EP2005/010759, filed on Oct. 6, 2005.

(30) Foreign Application Priority Data

Oct. 8, 2004 (DE) .......................... 10 2004 050 040

(51) Int. Cl.
*A61B 17/86* (2006.01)
*A61B 17/80* (2006.01)

(52) U.S. Cl. ......... 606/291; 606/286; 606/301; 606/305

(58) Field of Classification Search .......... 606/280–299, 606/301–321; 411/403, 970, 999
See application file for complete search history.

(56) References Cited

U.S. PATENT DOCUMENTS

| | | | |
|---|---|---|---|
| 5,100,272 A | 3/1992 | Jadoul | |
| 5,688,093 A | 11/1997 | Bowers | |
| 5,713,900 A | 2/1998 | Benzel | |
| 5,735,853 A | 4/1998 | Olerud | |
| 5,902,303 A * | 5/1999 | Eckhof et al. ................... | 606/60 |
| 5,904,683 A | 5/1999 | Pohndorf | |
| 6,039,740 A | 3/2000 | Olerud | |
| 6,117,173 A | 9/2000 | Taddia | |
| 6,241,730 B1 | 6/2001 | Alby | |

(Continued)

FOREIGN PATENT DOCUMENTS

| | | |
|---|---|---|
| CH | 672245 A5 | 11/1989 |
| DE | 4400497CI | 6/1995 |

(Continued)

OTHER PUBLICATIONS

U.S. Appl. No. 12/841,531, Non Final Office Action mailed Oct. 2, 2012, 14 pgs.

*Primary Examiner* — Kevin T Truong
*Assistant Examiner* — Michael T Schaper
(74) *Attorney, Agent, or Firm* — RatnerPrestia

(57) ABSTRACT

In order to improve a bone screw with a shaft defining a longitudinal axis and with a head which can be brought into engagement with a bone screw receiving means of a bone plate for the releasable connection of the bone screw to the bone plate, wherein a securing element for securing a connection between the bone screw and the bone plate is provided, wherein the bone screw can be brought from a position of engagement, in which the bone screw is held on the bone plate, into a release position, in which the bone screw can be released from the bone plate, wherein the securing element can be brought from a non-securing position, in which the bone screw can be brought into the release position, into a securing position for securing the connection between the bone screw and the bone plate, in which the bone screw takes up the position of engagement, such that a bone plate can be fixed to bone parts more easily and more securely it is suggested that the securing element be supported on the bone screw so as to be movable.

37 Claims, 7 Drawing Sheets

U.S. PATENT DOCUMENTS

| | | |
|---|---|---|
| 6,261,291 B1 | 7/2001 | Talaber |
| 6,280,131 B1 | 8/2001 | Ellis |
| 6,524,238 B2 | 2/2003 | Velikaris |
| 6,613,053 B1 | 9/2003 | Collins |
| 6,702,817 B2 | 3/2004 | Beger |
| 6,730,091 B1 | 5/2004 | Pfefferle |
| 7,048,739 B2 | 5/2006 | Konieczynski |
| 2002/0120273 A1 | 8/2002 | Needham |
| 2003/0078583 A1 | 4/2003 | Biedermann |
| 2003/0144666 A1* | 7/2003 | Bagga et al. ............ 606/61 |
| 2003/0199876 A1 | 10/2003 | Brace |
| 2003/0208204 A1 | 11/2003 | Bailey |
| 2004/0030336 A1 | 2/2004 | Khanna |
| 2006/0122605 A1 | 6/2006 | Suh |
| 2006/0167456 A1 | 7/2006 | Johnston |
| 2009/0192549 A1 | 7/2009 | Sanders |

FOREIGN PATENT DOCUMENTS

| | | |
|---|---|---|
| DE | 19545612AI | 6/1997 |
| DE | 19702201CI | 8/1998 |
| DE | 10152094AI | 5/2003 |
| EP | 0809974 A2 | 12/1997 |
| EP | 995404 A1 | 4/2000 |
| EP | 1306058 A2 | 5/2003 |
| EP | 1346697 A2 | 9/2003 |
| WO | 8803781 | 6/1988 |
| WO | 94026193AI | 11/1994 |
| WO | 9722306AI | 6/1997 |
| WO | 9956653 | 11/1999 |
| WO | 0066012AI | 11/2000 |

* cited by examiner

BONE SCREW

RELATED APPLICATIONS

This application is a continuation of U.S. application Ser. No. 11/732,752 filed on Apr. 4, 2007, which is a continuation of International Patent Application No. PCT/EP2005/010759 filed on Oct. 6, 2005 and designating the United States, which claims priority to German Application No. 10 2004 050 040, filed on Oct. 8, 2004. The contents of all of the foregoing related applications are incorporated by reference herein in their entireties for all purposes.

BACKGROUND OF THE INVENTION

The present invention relates to a bone screw with a shaft defining a longitudinal axis and with a head which can be brought into engagement with a bone screw receiving means of a bone plate for the releasable connection of the bone screw to the bone plate, wherein a securing element is provided for securing a connection between the bone screw and the bone plate, wherein the bone screw can be brought from a position of engagement, in which the bone screw is held on the bone plate, into a release position, in which the bone screw can be released from the bone plate, wherein the securing element can be brought from a non-securing position, in which the bone screw can be brought into the release position, into a securing position for securing the connection between the bone screw and the bone plate, in which the bone screw takes up the position of engagement.

Bone screws of the type described at the outset are used in surgery to fix bone plates to bone parts of a human or animal body. The advantage of these screws is the fact that the position of engagement can be locked and so the bone plate cannot become disconnected from the bone screw or screws when stressed. Locking elements are known, for example, which are arranged on the bone plate and are pushed over the head of the bone screw already screwed in. This has the disadvantage that a securing element must be provided at every opening in the bone plate. If, however, not all the bone screw receiving means of the bone plate are required, the securing elements arranged at the bone screw receiving means which are not used are also, strictly speaking, superfluous. In addition, it must be ensured prior to the insertion of the bone plate that all the securing elements are in the non-securing position. If this is not the case, all the securing elements must be transferred from the securing position into the non-securing position during the operation which increases the operation time unnecessarily.

SUMMARY OF THE INVENTION

In accordance with the invention, a bone screw of the type described at the outset is suggested, wherein the securing element is supported on the bone screw so as to be movable.

As a result of the movable supporting of the securing element on the bone screw, the number of securing elements required is merely the same as the number of bone screws actually used for securing the bone plate. Moreover, it is ensured that each bone screw comprises its own securing element. It is favorable, in particular, when the securing element is supported on the bone screw so as to be movable in a captive manner. As a result, it is possible to avoid the securing element being transferred easily and simply from the securing position into the non-securing position and vice versa, in particular, in the case of very small bone screws such as those used, for example, in the cervical area of the spinal column. Moreover, it cannot be lost in an operation area.

A particularly simple construction of the bone screw results when it is designed so as to be rotationally symmetric or essentially rotationally symmetric in relation to the longitudinal axis.

In the position of engagement, the head preferably has a maximum external dimension transversely to the longitudinal axis and, in the release position, an external dimension which is reduced in size in comparison with the maximum external dimension. This allows the head to be brought into engagement with part of the bone plate, for example, the bone screw receiving means in the position of engagement and out of engagement with it in the release position. The head can have any optional shape, for example, with a square or round cross section transversely to the longitudinal axis.

Particularly with a round cross section of the head, it is advantageous when the head has a maximum external diameter transversely to the longitudinal axis in the position of engagement and an external diameter which is reduced in size in comparison with the maximum external diameter in the release position. For example, the head can be pressed together proceeding from the position of engagement in order to transfer the bone screw into the release position or, however, also be spread apart from the release position in order to transfer the bone screw into the position of engagement. It would, therefore, be conceivable to design the bone screw such that it takes up either the position of engagement or the release position without any influence of external forces.

A connection between the bone screw and the bone plate can be provided in a particularly simple manner when the head bears a first snap-in element which can be interlocked with a second snap-in element arranged on the bone plate in the position of engagement. The two snap-in elements can therefore be in engagement in the position of engagement, in particular, engage in one another in a form-locking manner.

The construction of the bone screw may be configured in a particularly simple manner when the first snap-in element is an annular groove which extends in circumferential direction and is open radially or an annular projection which extends in circumferential direction and protrudes radially outwards. The annular groove may, for example, accommodate a corresponding projection or corresponding projections on the bone plate. The protruding annular projection can be brought into engagement with a corresponding groove on the bone plate in order to provide a connection between the bone screw and the bone plate.

In accordance with a preferred embodiment of the invention, it may be provided for the securing element to be held in the securing position in a basic position of the bone screw, in which no external forces act on the bone screw. This has the advantage that a physician does not have to think about locking the bone screw since it takes up the securing position in a basic position. As a result, the operating time is shortened and mistakes avoided. Furthermore, the number of instruments required is also reduced since no special instrument for the securing element is required. In order to keep the securing element in the securing position, the bone screw can also be designed such that no forces act on the securing element in the securing position; the securing element, is, therefore, held free from forces.

It is advantageous when the securing element is held in the securing position under tension. In order to transfer the securing element from the securing position into the non-securing position contrary to the tensioning, a certain releasing force must, therefore, be applied. Since the securing element is held under tension, it is automatically transferred back again from the non-securing position into the securing position. A physician need not, therefore, lock each bone screw individually; the bone screw locks itself as a result of the special configuration.

It is advantageous when at least one holding element is provided for holding the securing element in the securing position when it is supported, on the one hand, on the shaft and, on the other hand, on the securing element. The securing element can be arranged, in particular, in a cavity or a recess of the shaft, in which it is, in addition, protected.

Defined holding forces may be generated in different positions of the securing element when the holding element is an elastic element.

The construction of the bone screw is particularly simple when the holding element is a helical spring or a plate spring or stack of plate springs. A desired holding force, with which the securing element is held in the securing position or is also held in this position under tension, may be adjusted in a simple manner.

In accordance with a preferred embodiment of the invention, it may, in addition, be provided for the holding element to be of such a design that an external dimension and/or a volume of the holding element is variable due to variation of at least one state parameter in the surroundings of the bone screw. For example, pressure can be increased in the surroundings of the bone screw, as a result of which the volume of the holding element is increased or decreased. As a result of the change in the external dimension and/or the volume of the holding element, the securing element may be transferred from the non-securing position into the securing position and/or vice versa.

It is favorable when the at least one state parameter is ambient temperature, ambient pressure, osmotic pressure or humidity of the surroundings. This allows the state of the holding element to be changed, in particular, an outer dimension and/or a volume thereof as a result of alteration to the specified or also additional physical parameters in the surroundings of the bone screws.

The holding element is favorably produced from a memory metal. In particular, it is thus possible, for example, to transfer the securing element from the securing position into the non-securing position as a result of cooling or heating and vice versa, again due to heating or cooling.

In addition, the securing element can be moved in a simple manner when the holding element is inflatable by means of a fluid. For example, the fluid can be air, compressed air or a biocompatible liquid.

In order to be able to utilize alterations in an osmotic pressure, in particular, in order to vary the holding element in its size, it is favorable when the holding element has an interior space which is in fluid communication with the surroundings of the bone screw via a semi-permeable membrane. This allows, for example, water to be diffused into the interior space of the holding element as a function of a solvent concentration in the surroundings of the bone screw.

Securing of the bone screw in the position of engagement may be brought about particularly easily when the securing element is supported on the shaft so as to be displaceable parallel to the longitudinal axis.

In order to also facilitate, in particular, a captive supporting of the securing element on the bone screw, it is advantageous when the shaft has a securing element receiving means and when the securing element is supported in the securing element receiving means.

The bone screw is particularly simple to produce when the securing element receiving means is a blind hole. The securing element can then be introduced, first of all, into the securing element receiving means through an opening in the blind hole but cannot exit again out of the bone screw on the other side of the recess. The blind hole is preferably arranged such that an opening thereof is arranged in the area of the head of the bone screw.

The securing element is advantageously held in the securing element receiving means in a non-rotational form-locking manner. This allows a force to be passed to the bone screw for turning the same into a bone part via the securing element and to be transferred to the shaft of the bone screw as a result of the non-rotational form-locking design of the securing element receiving means. It will, in particular, be possible as a result to provide a tool adapter for a screw-in tool of the bone screw on the securing element itself.

The stability of the bone screw is increased as a whole when the securing element has a securing element section which is designed in the shape of an external polyhedron and when the securing element receiving means has a securing element receiving means section which is designed in the shape of an internal polyhedron corresponding to the external polyhedron. For example, the external polyhedron can be designed as a square, hexagon or octagon. A transfer of force following a rotation of the securing element on the shaft of the bone screw can be optimized in this way.

So that the securing element can be held on the bone screw in a captive manner, it is advantageous when the securing element, after the insertion of the securing element into the securing element receiving means, can be moved in an axial direction between a stop acting in a distal direction and a stop acting in a proximal direction. The securing element can, therefore, be moved in an axial direction against the stop, which acts in a proximal direction and on which it abuts, for example, in the non-securing position. Furthermore, the securing element can be moved against the stop acting in a distal direction and abut on it when it takes up, for example, the securing position.

So that no tension results at the bone screw in the position of engagement which can lead to damage thereto as a result of permanent stressing, it is advantageous when the bone screw takes up the position of engagement without any action of external forces. This is favorable, as described, since, for example, in the case of bone screws with a head which is spread apart in the position of engagement, the head is always subject to tension and elements which can be spread apart can break as a result of permanent stressing.

In order to realize a transfer of the bone screw from the position of engagement into the release position and vice versa in a simple manner, it is advantageous when the first snap-in element is supported on the bone screw so as to be movable in a radial direction. It can, therefore, be moved in a radial direction away from the longitudinal axis or towards it. The snap-in elements may, in particular, be supported on the bone screw so as to be displaceable or pivotable.

A connection between the bone screw and the bone plate may be provided in a simple manner when the head comprises a plurality of locking elements which can be moved transversely to the longitudinal axis and are in engagement with the bone plate in the position of engagement.

In principle, it would be conceivable to provide a different connection instead of a snap-in connection between the bone screw and the bone plate, for example, a bayonet connection. If, however, a snap-in connection is desired, it is favorable when the locking elements bear the first snap-in element. The first snap-in element can then be brought into engagement with the second snap-in element on the bone plate as a result of movement of the locking element or the locking elements, respectively.

If the bone screw has a securing element receiving means, at least part of the bone screw is of a sleeve-like design. It is advantageous when the head has tab-like wall sections separated by slots extending parallel to the longitudinal axis and when the wall sections form the locking elements. In order to produce the locking elements, only the head of the bone screw must, for example, be provided with slots. Four, five or six locking elements are advantageously provided and these can be formed by four, five or six slots which are distributed symmetrically over a circumference of the bone screw.

It is favorable when the locking elements take up the position of engagement in a basic position, in which no external forces act on the bone screw. The locking elements must, therefore, be moved only for the purpose of transferring the bone screw from the position of engagement into the release position and are subject to tension only for this short time. In the position of engagement, they are, however, essentially without tension and so there is no risk of the locking elements being able to break as a result of permanent stressing.

In order to transfer the bone screw from the position of engagement into the release position, it may be provided for the locking elements to be moved radially in a direction towards the longitudinal axis. Therefore, the locking elements can favorably be moved radially outwards from the position of engagement in order to insert the securing element into the securing element receiving means. This means, in other words, that the securing element spreads the locking elements apart and, with them, for example, a head of the bone screw during its insertion into the securing element receiving means. After insertion of the securing element into the securing element receiving means, the locking elements can return to their original shape, in which they take up the position of engagement. The securing element is then, with this embodiment, held in the securing element receiving means in a captive manner. In order to remove the securing element from the securing element receiving means, the locking elements must be pivoted again radially outwards in order to release the opening of the securing element receiving means to such an extent that the securing element can be withdrawn from it.

In order to hold the securing element on the bone screw in a captive manner, it is favorable when a second snap-in device comprising a third snap-in element and a fourth snap-in element interacting with the third snap-in element is provided, when the securing element and the head each bear a snap-in element and when the second snap-in device takes up a snap-in position after the insertion of the securing element into the securing element receiving means. A snap-in connection preferably results, therefore, when the securing element is inserted into the securing element receiving means. In order to release the snap-in connection, at least one of the two snap-in elements must be moved relative to the other. If this does not occur, the securing element is held in the securing element receiving means in a captive manner.

A particularly simple construction of the bone screw results when the third snap-in element is a snap-in nose which acts in a proximal direction and projects radially outwards and when the fourth snap-in element is a snap-in edge which projects radially inwards and acts in a distal direction. The snap-in nose and the snap-in edge can engage behind one another in the snap-in position in order to form a snap-in connection and thus secure the securing element in the securing element receiving means.

A relative movement of the third snap-in element and the fourth snap-in element may be realized in a simple manner in that the locking elements bear the fourth snap-in element. As a result, the fourth snap-in element can be moved relative to the third during movement of the locking elements and, in addition, be brought into engagement or out of engagement.

Advantageously, the third or the fourth snap-in element forms the proximal stop and these elements abut on one another in the securing position. It is conceivable, in particular, for the holding element to press the securing element in a proximal direction so that the third or fourth snap-in element abuts on the proximal stop which acts in a distal direction.

In order to facilitate the assembly of the bone screw and, in particular, to make instruments for the assembly of the bone screw superfluous, it is advantageous when a slide-on surface adjoins the third or the fourth snap-in element, the respectively other snap-in element being able to slide on this surface during the insertion of the securing element into the securing element receiving means. For example, the slide-on surface can extend in a distal direction starting from the third snap-in element arranged on the securing element so that the fourth snap-in element arranged on the head of the bone screw can slide onto it during the insertion of the securing element into the securing element receiving means and, as a result, be moved outwards in a radial direction until it engages behind the third snap-in element, whereby it can be moved again in a radial direction towards the longitudinal axis. The securing element can, therefore, be secured in the securing element receiving means in this way.

The stability of the bone screw may be increased when the securing element is designed in the shape of a set bolt with a bolt shaft and a bolt head.

The construction of the securing element is particularly simple when the bolt shaft forms the securing element section which is designed in the shape of an external polyhedron.

In order to hold the securing element in the securing element receiving means so as to be captive but movable in a simple manner, it is advantageous when the bolt head bears the third snap-in element. For example, the third snap-in element can be designed in the shape of an annular projection which protrudes radially outwards and forms a stop surface which extends in a proximal direction transversely to the longitudinal axis and is adjoined by a slide-on surface tapering conically in a distal direction.

In order to be able to screw the bone screw into a bone part in a simple manner, it is favorable when the bone screw has a tool element adapter which can be brought into engagement with a screw-in tool for the screwing in of the bone screw.

The securing element preferably bears the tool adapter. This has the advantage that two functions can be exercised at the same time with the screw-in tool. On the one hand, the screw-in tool can, in certain embodiments, transfer the securing element from the securing position into the non-securing position, for example, also contrary to the tension generated by a holding element. On the other hand, the entire bone screw can be turned in with the screw-in tool, for example, when the securing element is held in the securing element receiving means in a non-rotational, form-locking manner.

In principle, it would be conceivable for the tool adapter to be designed in the shape of a projection. It is, however, favorable when the tool adapter is a recess. In this respect, it may be advantageous when the recess is designed in the shape of a slot, a polyhedron or a star-shaped cavity.

In order to increase the stability of the bone screw, it is advantageous when the head and the shaft are designed in one piece.

In accordance with a preferred embodiment of the invention, it may be provided for the shaft to be provided with an external thread. The external thread can, in particular, be a self-cutting bone thread. A secure hold of the bone screw in the bone part is ensured as a result of the external thread.

The object specified at the outset is also accomplished in accordance with the invention, in an implant system comprising at least one bone plate with at least one bone screw receiving means and at least one bone screw which can be brought into engagement with the bone screw receiving means in a position of engagement for the releasable connection of the bone screw to the bone plate, in that the bone screw is one of the bone screws described above. This results in the advantages already explained for the connection of bone parts to the bone plate of the implant system, wherein the bone plate can be secured to the bone part with the at least one bone screw.

The following description of preferred embodiments of the present invention serves to explain the invention in greater detail in conjunction with the drawings.

DETAILED DESCRIPTION OF THE INVENTION

Figure 1:
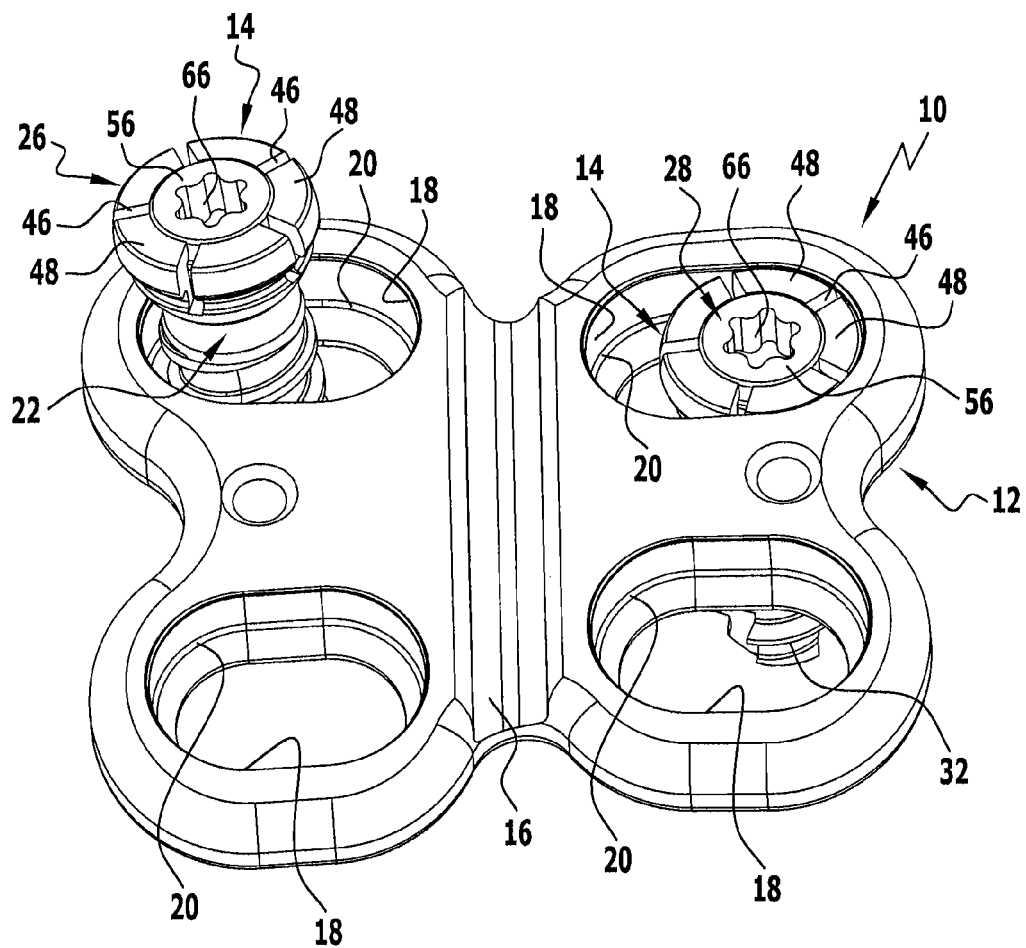
FIG. 1 shows a perspective view of an implant system comprising a bone plate and two bone screws.
Figure 2:
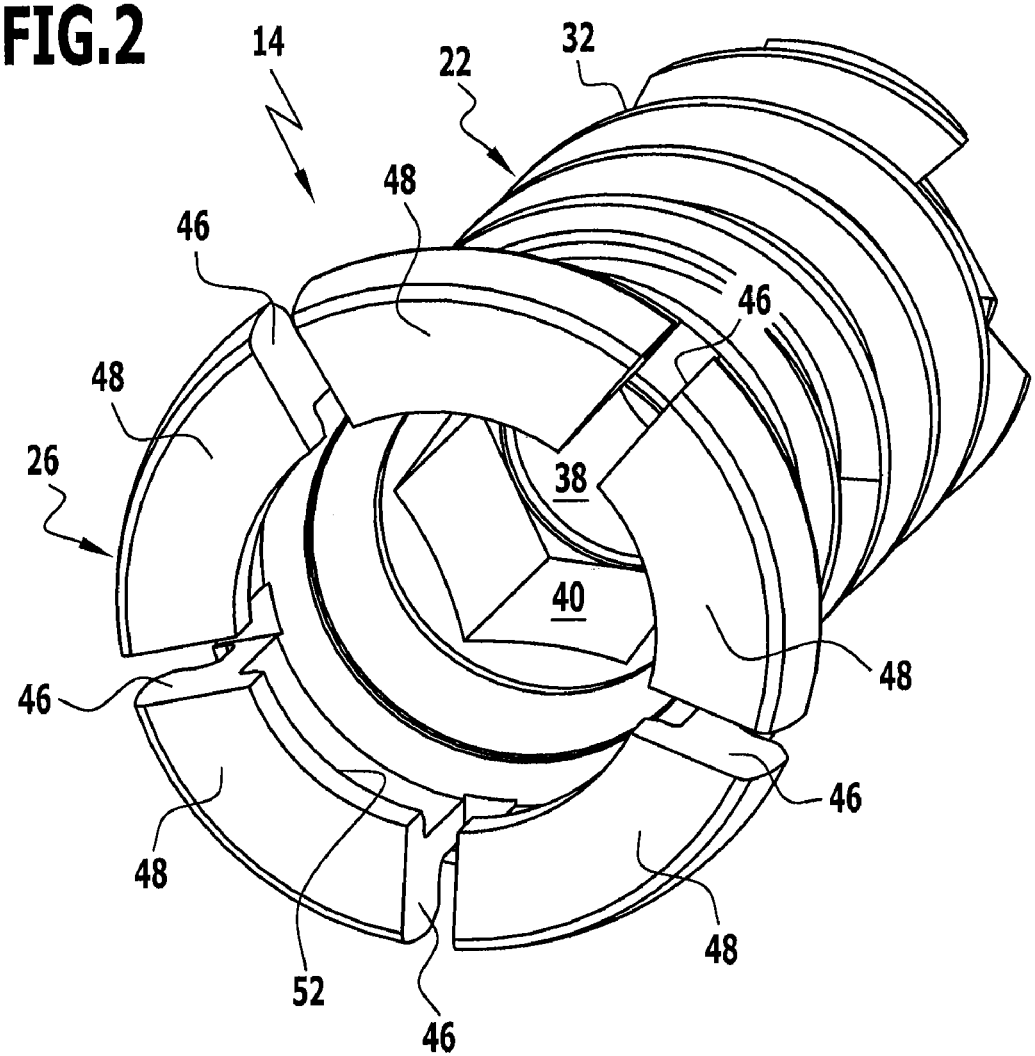
FIG. 2 shows a perspective view of a proximal end of a bone screw from FIG. 1 prior to the insertion of a securing element.

An implant system provided altogether with the reference numeral 10 and comprising a bone plate 12 and two self-locking bone screws 14 is illustrated in FIG. 1.

The bone plate 12 illustrated in FIG. 1 serves in the first place as illustration; it does not represent any limitation of the present invention. In principle, all types of bone plate, which have at least one opening for a bone screw, would be conceivable in conjunction with the present invention.

The bone plate 12 is flat and shaped like a clover leaf with outer edges rounded on all sides. A groove-like recess 16, which separates, so-to-speak, two respective pairs of leaves of the bone plate 12 from one another, is provided approximately in the center. Altogether, the bone plate 12 is designed in one piece. An opening 18 in the form of an elongated hole is provided in the area of each corner of the bone plate 12, wherein longitudinal directions of the openings 18 are aligned essentially parallel to one another. A maximum extension of the openings 18 is oriented transversely to the longitudinal direction of the recess 16 so that a minimal inner dimension of the openings 18 essentially parallel to the longitudinal direction of the recess 16 is predetermined. Inner edges 20 of the openings 18 are curved concavely in the direction towards a center of the respective opening 18 so that edges limiting the opening 18 project radially inwards not only on the upper side of the bone plate 12 but also on its underside. The openings 18 therefore form, with their concave edges 20, recessed areas in the bone plate 20 which are essentially shaped like hollow caps.

The bone screws 14, which, in the form of a first embodiment, will be explained in greater detail in the following in conjunction with FIGS. 1 to 5, serve to secure the bone plate 12 on bone parts which are not illustrated.

The bone screw 14 is essentially designed in three parts. It comprises a shaft 22, which defines a longitudinal axis 23, a screw tip 24 on the distal side and a screw head 26 on the proximal side, as well as a securing element in the form of a locking pin 28 and a helical spring 30 serving as a holding element. The shaft 22 is provided over approximately three quarters of its length, starting from its screw tip 24, with an external thread 32 which is preferably designed to be self-cutting. An outer contour or cover end of the screw head 26 is essentially of a cap-like design and adapted to the recessed area of the opening 18 formed by the inner edge 20, whereby a polyaxial adaptation of the screw head 26 in the recessed opening 18 is made possible.

Proceeding from its proximal end, the shaft 22 is provided with a blind hole 34 which forms a securing element receiving means and the base 36 of which on the distal side points in the direction towards the proximal end of the bone screw 14. Proceeding from the base 36, a hollow cylindrical section 38 extends over approximately one third of the overall length of the blind hole 34 and the helical spring 30, which is supported on the base 36 with its end on the distal side, is inserted into this section. An inner hexagonal section 40, which forms approximately a central third of the blind hole 34, adjoins the hollow cylindrical section 38. The interior diameter of the hollow cylindrical section 38 is somewhat smaller than an interior dimension of the inner hexagonal section 40 and so a distal stop 42 formed by an annular surface pointing in a proximal direction is formed in the area of transition between the hollow cylindrical section 38 and the inner hexagonal section 40.

Approximately the proximal third of the shaft 22 forms the screw head 26 which has an external diameter increased in size in comparison with the shaft section provided with the external thread 32. The screw head 26 is provided on an outer side with a circumferential annular groove 44. In order to be able to vary the screw head 26 in its external diameter, it is provided symmetrically around its circumference with five slots 46 extending parallel to the longitudinal axis 23 and so altogether five segments 48 of the screw head 26, which form locking elements, are formed. The segments 48 form tab-like sleeve sections which can be pivoted in a radial direction, i.e., in a direction towards the longitudinal axis 23 or away from it. A desired pivotability may be adjusted via the depth of the annular groove 44 which forms a weakened area and facilitates movability of the segments 48. An opening 50 in the blind hole 34 is provided with an annular flange 52 which projects radially inwards towards the longitudinal axis 23 and is interrupted by the slots 46 in the same way as the annular groove 44. The annular flange 52 forms a narrowing of the internal diameter of the blind hole 34. Furthermore, it has an annular stop surface 54 which points in a distal direction and forms a stop acting in a distal direction on the proximal side.

Proceeding from the inner hexagonal section 40, an interior diameter of the blind hole 34 widens as far as a maximum internal diameter which extends in the interior in the area of the annular groove 44 as far as the stop surface 54.

The locking pin 28 is, altogether, shaped in the form of a set bolt with a head 56 and a bolt shaft 58 designed in the shape of an external hexagon and corresponding to the shape of the interior hexagonal section 40. The head 56 which is of a larger size in its external diameter in relation to the bolt shaft 58 has a snap-in lip 60 which extends in circumferential direction, projects radially outwards and comprises an annular stop surface 62 which points in a proximal direction and a slide-on surface 64 which extends in a distal direction from the outer edge of the stop surface 62 and tapers conically.

Figure 4:
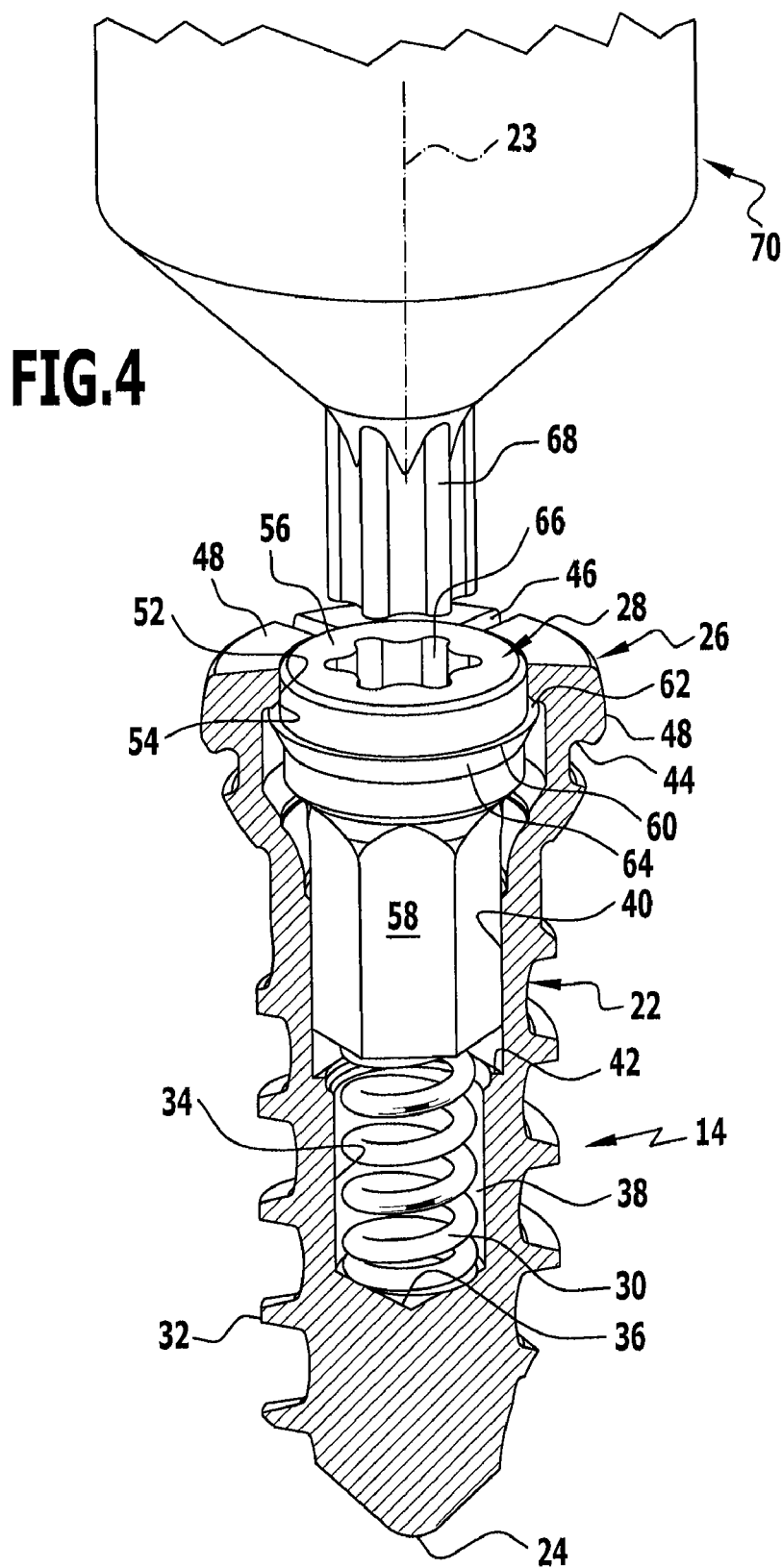
FIG. 4 shows a partially cutaway side view of the bone screw with the securing element in the position of engagement.
Figure 5:
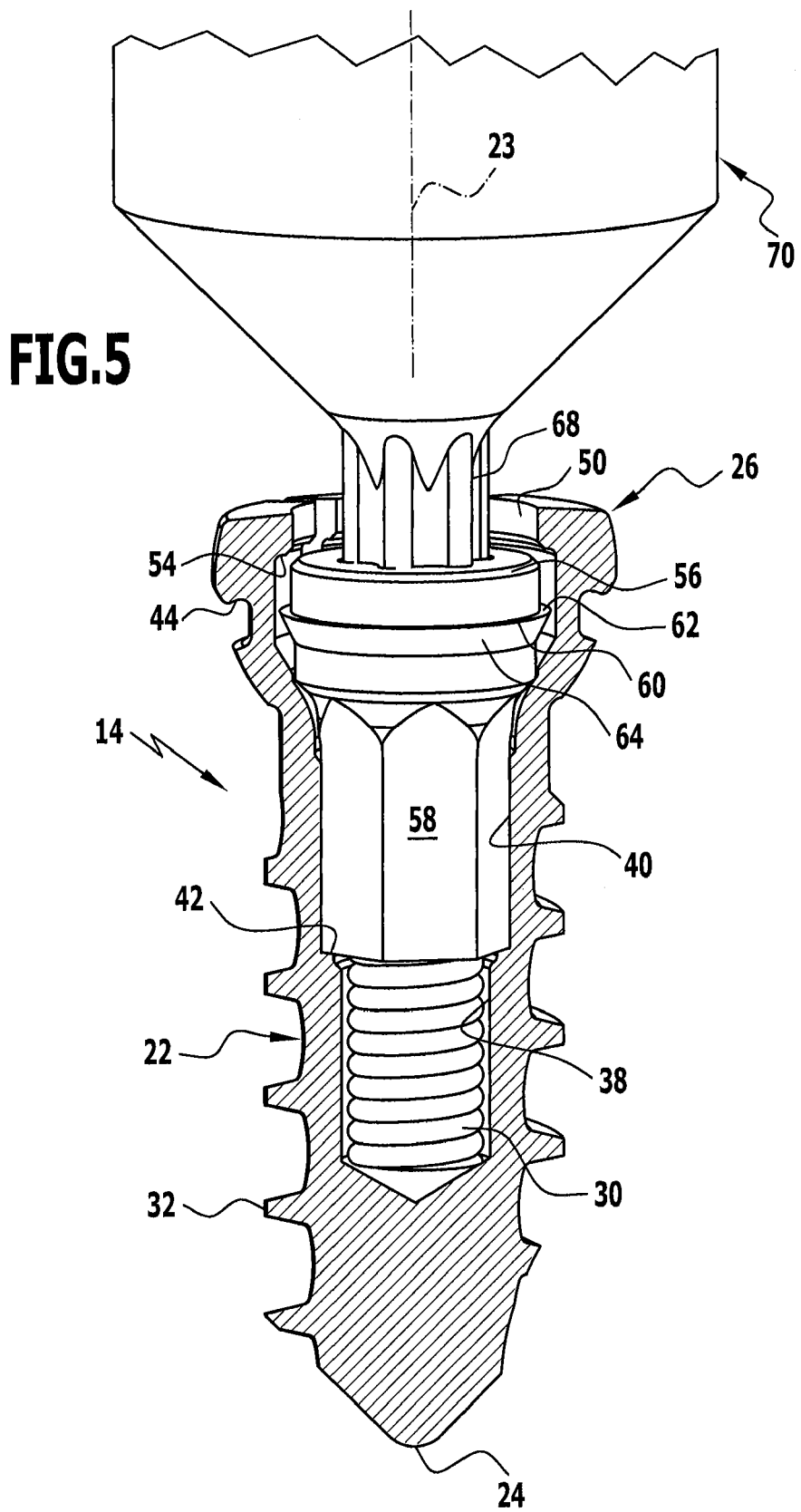
FIG. 5 shows a view similar to FIG. 4, wherein the bone screw takes up the release position.

A star-shaped recess is provided on the head and this points in a proximal direction, is like a blind hole and serves as a tool receiving means 66 for accommodating a corresponding tool tip of a screw-in tool 70, the distal end of which is illustrated in FIGS. 4 and 5.

Figure 3:
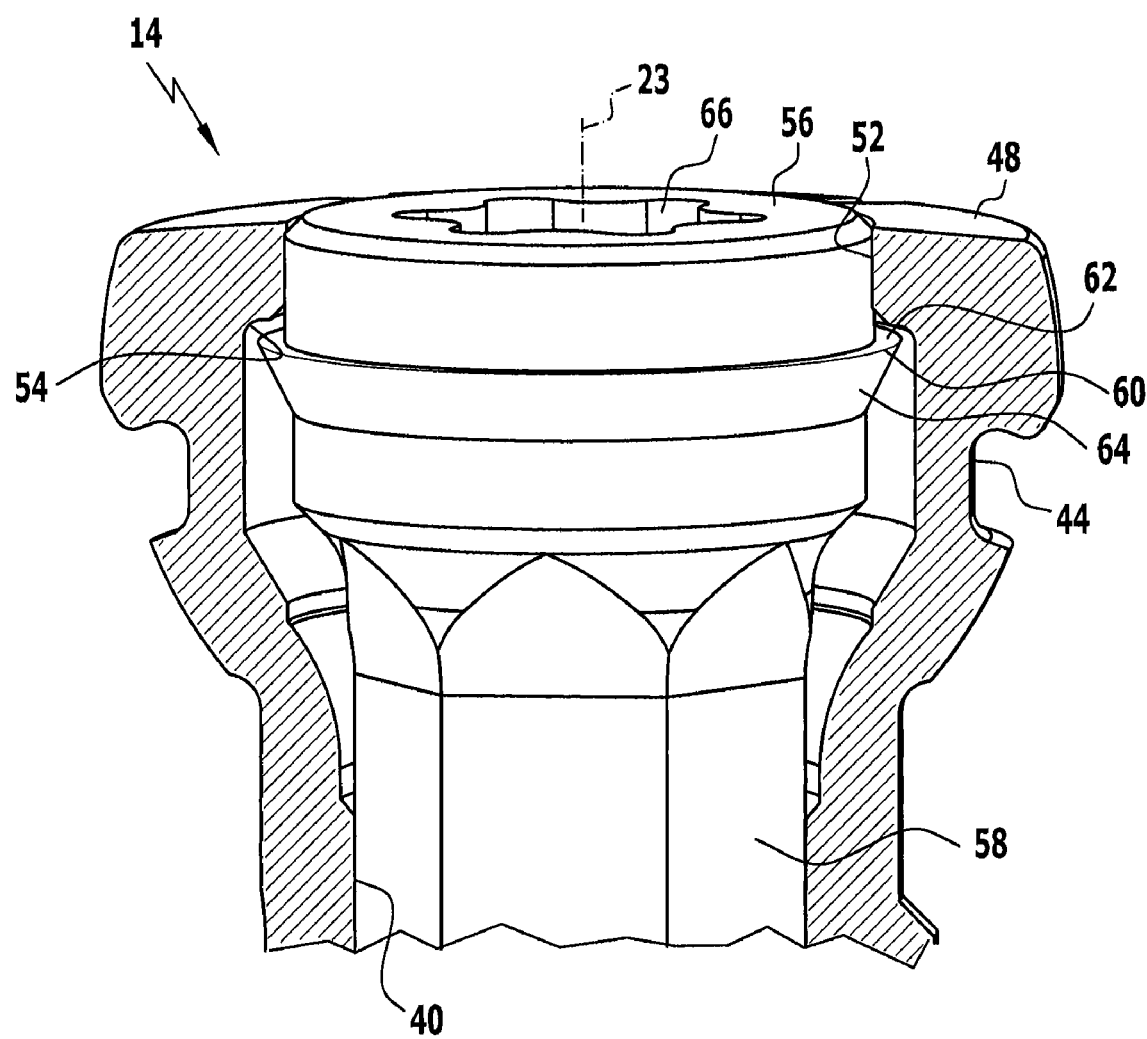
FIG. 3 shows a partially cutaway side view of a proximal end of a bone screw from FIG. 1 in the position of engagement.

The procedure for assembling the three-part bone screw 14 is as follows. First of all, the helical spring 30 is inserted into the blind hole 34 through the opening 50 until a distal end of the helical spring 30 abuts on the base 36. The next step is to push the locking pin 28 with its bolt shaft through the opening 50 until the annular flange 52 abuts on the slide-on surface 64. For the complete insertion of the locking pin 28 into the blind hole 34, the segments 48 must now be spread radially outwards. This occurs as a result of the exertion of force on the locking pin 28 in a distal direction. The annular flange 52 on the segments 48 slides on the slide-on surface 64 such that the segments 48 are pivoted radially outwards and spring back radially inwards behind the snap-in lip 60 as soon as the stop surface 62 engages behind the stop surface 54 on the annular flange 52. A proximal end of the helical spring 30 abuts on the distal end of the bolt shaft 58 and presses the locking pin 48 in a proximal direction and thus keeps the stop surfaces 54 and 62 in abutment on one another. The bone screw 14 then takes up its position of engagement, as illustrated in FIGS. 1, 3 and 4.

In order to screw the bone screw 14 into a bone part which is not illustrated and to secure the bone plate 12 on the same, the bone screw 14 with its shaft 22 provided with an external thread 32 is first of all pushed through the opening 18. If the tool tip 68 engages in the tool receiving means 66, the locking pin 28 is moved in a distal direction contrary to the spring force of the helical spring 30 until the distal end of the bolt shaft 58 abuts on the stop 42. The locking pin 28 then takes up the non-securing position illustrated in FIG. 5.

As a result of the non-rotational, form-locking design of the inner hexagonal section 40 and the bolt shaft 58, torque introduced into the head 56 by the tool tip 68 can be transferred to the shaft 22 of the bone screw 14. The bone screw 14 can be screwed ever deeper into the bone part, namely to such an extent until the screw head 26 with the pivotable segments 48 abuts on the upper, annular edge of the opening 18. The segments 48 slide on the upper edge when the bone screw 14 is screwed further in and are pivoted radially inwards until a proximal end of the bone screw 14, i.e., the screw head 26 can dip completely into the recessed opening 18. The segments 48 then spring back radially outwards and again take up their position of engagement. The screw head 26 is held in the recessed opening 18 in this way but not yet secured.

It is possible for the screw head 26 to dip into the recessed opening 18 only when the locking pin 28 takes up the non-securing position illustrated in FIG. 5. If the bone screw 14 is seated as desired in the bone, a surgeon will remove the screw-in tool 70. As a result of the restoring force exerted by the helical spring 30 on the locking pin 28, this is moved in a proximal direction until the stop surface 62 of the snap-in lip 60 again abuts on the stop surface 54. The head 56 of the locking pin 28 is then seated flush between the segments 48 and forms a flat termination of the bone screw 14 on the proximal side.

The bone screw 14 takes up the position of engagement without any influence from external forces and is secured in the position of engagement by the locking pin 28 held in the securing position by means of the helical spring 30.

Figure 6:
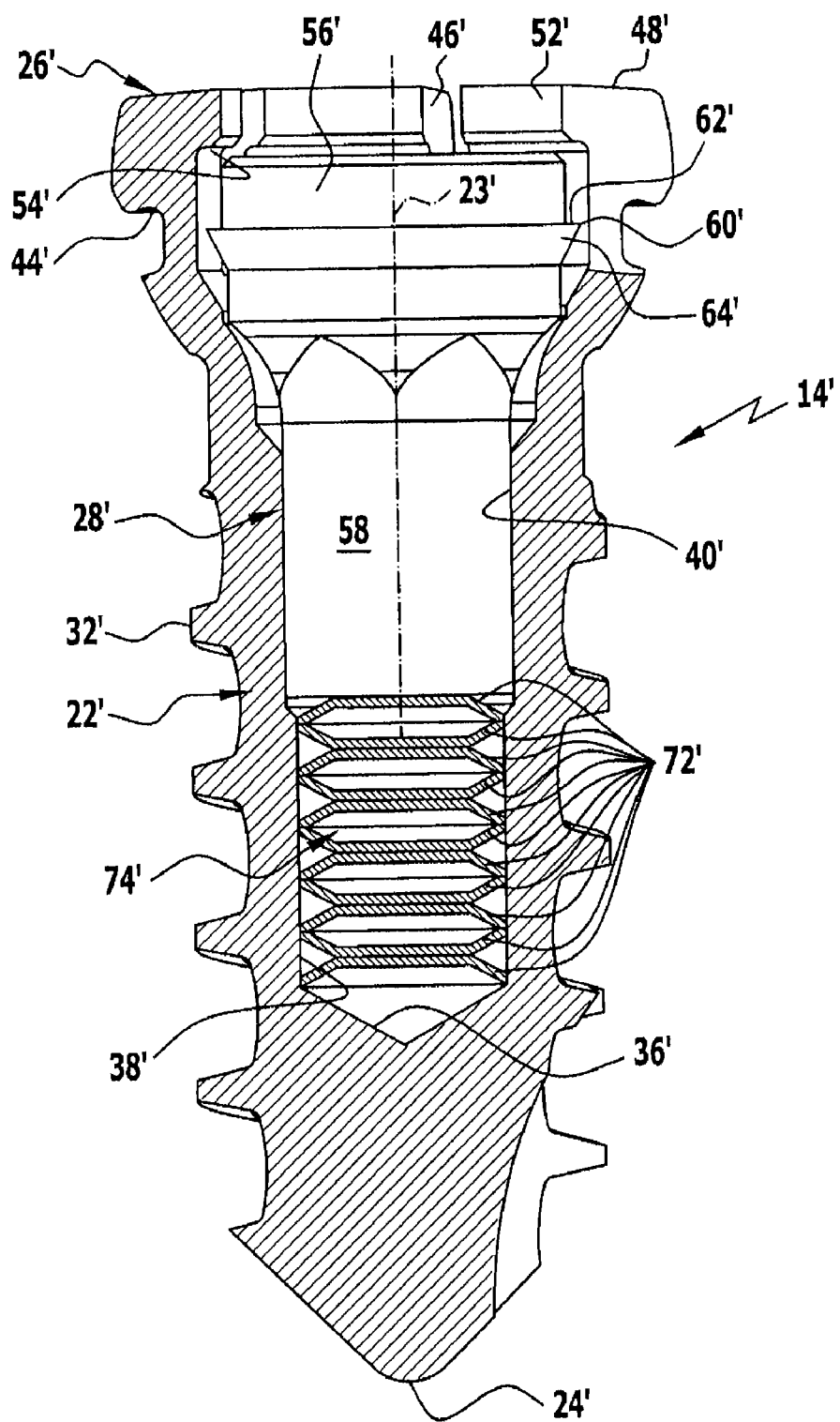
FIG. 6 shows a partially cutaway side view through a second embodiment of a bone screw in the release position.

In FIG. 6, a second embodiment of a bone screw provided altogether with the reference numeral 14' is illustrated. The bone screw 14' differs from the bone screw 14 illustrated in FIGS. 1 to 5 in that instead of the helical spring 30 a stack 74' of plate springs comprising altogether elf plate springs 72' is provided which is supported on the base 36' on the distal side and on the distal end of the bolt shaft 58' on the proximal side. All the remaining parts and elements of the bone screw 14' correspond to those of the bone screw 14 and so the same parts are also provided with the same reference numerals but with a superior case prime (') added in FIG. 6. The mode of operation of the bone screw 14' corresponds completely to that of the bone screw 14 described in conjunction with FIGS. 1 to 5.

Figure 7:
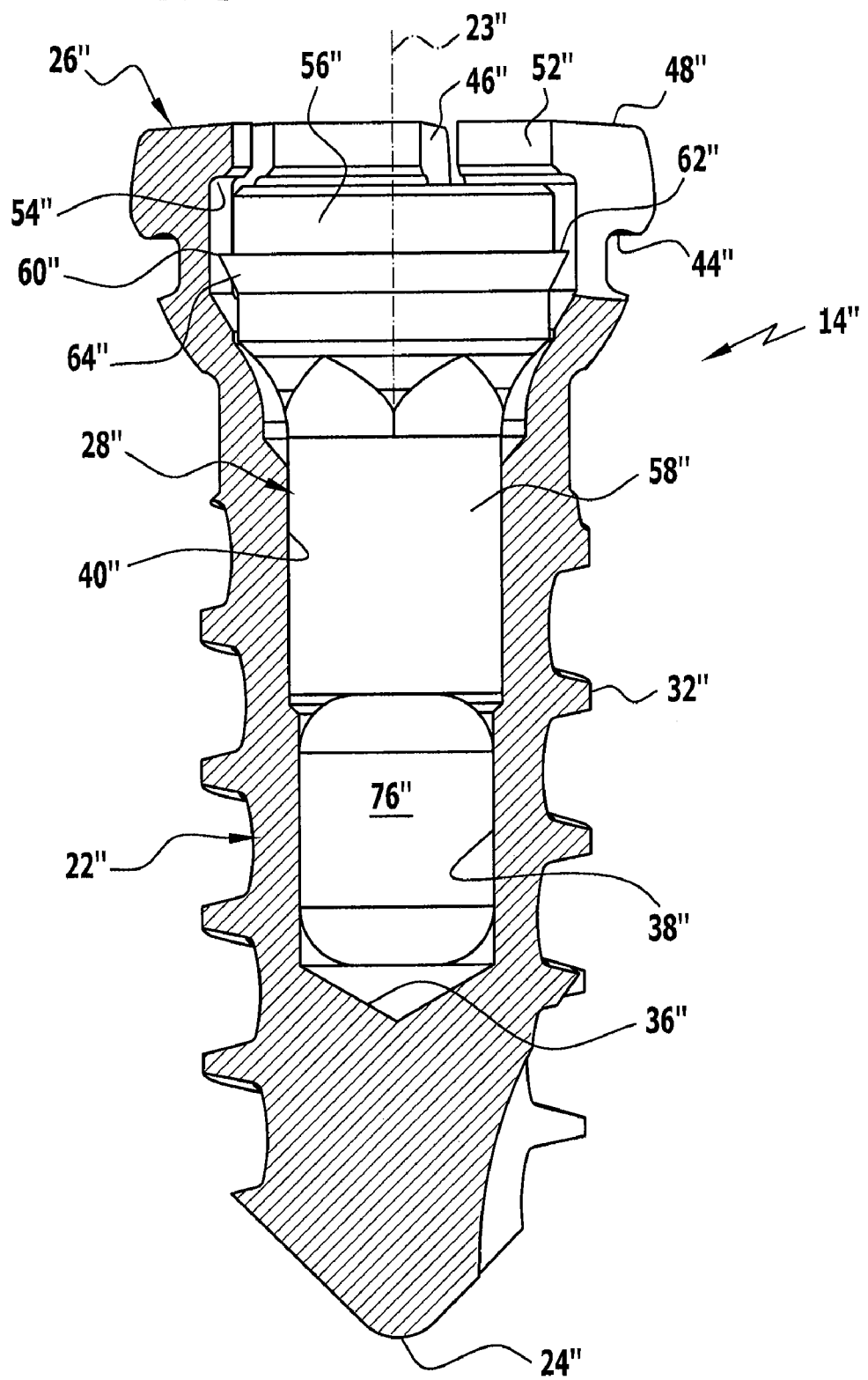
FIG. 7 shows a view similar to FIG. 6 of a third embodiment of a bone screw.

A third embodiment of a bone screw provided altogether with the reference numeral 14" is illustrated in FIG. 7. Instead of the helical spring 30 of the bone screw 14, a holding member 76" is provided for the bone screw 14". All the other parts and elements of the bone screw 14" correspond to those of the bone screw 14 and so identical reference numerals are used but with a double prime (") added.

The holding member 76" is variable in its volume in the embodiment illustrated. For this purpose, it has a sleeve which surrounds an element which is variable in expansion or shape and is produced from a memory metal. As a result of changes in temperature at the bone screw, the element expands or contracts so that the locking pin 28" can be transferred from the non-securing position illustrated in FIG. 7 into the securing position, in which the stop surfaces 54" and 62" abut on one another.

What is claimed is:

1. A bone screw with a shaft defining a longitudinal axis and a head adapted to be brought into engagement with a bone screw receiving means of a bone plate for the releasable connection of the bone screw to the bone plate, wherein a securing element is provided for securing a connection between the bone screw and the bone plate, wherein the bone screw is adapted to be brought from a position of engagement, the bone screw being held on the bone plate in said position, into a release position, the bone screw being releasable from the bone plate in said release position, wherein the securing element is adapted to be brought from a non-securing position, the bone screw being adapted to be brought into the release position in said non-securing position, into a securing position for securing the connection between the bone screw and the bone plate, the bone screw taking up the position of engagement in said securing position, wherein the securing element is supported on the bone screw so as to be movable, the bone screw further comprising at least one holding element, the at least one holding element exerting a biasing force on the securing element in the direction of the longitudinal axis to hold the securing element in the securing position, the head bearing a first snap-in element adapted to be interlocked with a second snap-in element arranged on the bone plate in the position of engagement, the shaft having a hole, the securing element being supported in the hole, the head comprising a plurality of locking elements movable transversely to the longitudinal axis, said locking elements being in engagement with the bone plate in the position of engagement, the bone screw further comprising a second snap-in device comprising a third snap-in element and a fourth snap-in element interacting with the third snap-in element, wherein the securing element and the head each bear a snap-in element and wherein the second snap-in device takes up a snap-in position after the insertion of the securing element into the hole, wherein the locking elements bear the fourth snap-in element.

2. A bone screw as defined in claim 1, wherein the bone screw is generally rotationally symmetric in relation to the longitudinal axis.

3. A bone screw as defined in claim 1, wherein in the position of engagement the head has a maximum external dimension transversely to the longitudinal axis and in the release position an external dimension reduced in size in comparison with the maximum external dimension.

4. A bone screw as defined in claim 3, wherein in the position of engagement the head has a maximum external diameter transversely to the longitudinal axis, and in the release position an external diameter reduced in size in comparison to the maximum external diameter.

5. A bone screw as defined in claim 1, wherein the first snap-in element is an annular groove extending in circumferential direction and being open radially or an annular projection protruding radially outward and extending in circumferential direction.

6. A bone screw as defined in claim 1, wherein the securing element is held in the securing position in a basic position of the bone screw, with no external forces acting on the bone screw in said basic position.

7. A bone screw as defined in claim 6, wherein the securing element is held in the securing position by an abutment.

8. A bone screw as defined in claim 6, wherein said holding element is supported on at least one of the shaft and on the securing element.

9. A bone screw as defined in claim 8, wherein the holding element is an elastic element.

10. A bone screw as defined in claim 8, wherein the holding element is designed in such a manner that an external dimension and/or a volume of the holding element is variable due to alteration to at least one state parameter in the surroundings of the bone screw.

11. A bone screw as defined in claim 10, wherein the at least one state parameter is ambient temperature, ambient pressure, osmotic pressure or humidity of the surroundings.

12. A bone screw as defined in claim 11, wherein the holding element is produced from a memory metal.

13. A bone screw as defined in claim 11, wherein the holding element has an interior space in fluid communication with the surroundings of the bone screw via a semi-permeable membrane.

14. A bone screw as defined in claim 1, wherein the securing element is supported on the shaft so as to be displaceable parallel to the longitudinal axis.

15. A bone screw as defined in claim 1, wherein the hole is a blind hole.

16. A bone screw as defined in claim 1, wherein the securing element is held in the hole in a non-rotational form-locking manner.

17. A bone screw as defined in claim 1, wherein the securing element has a securing element section designed in the shape of an external polyhedron and wherein the hole has a hole section designed in the shape of an internal polyhedron corresponding to the external polyhedron.

18. A bone screw as defined in claim 1, wherein following the insertion of the securing element into the hole the securing element is movable in an axial direction between a stop acting in a distal direction and a stop acting in a proximal direction.

19. A bone screw as defined in claim 1, wherein the bone screw takes up the position of engagement without any action of external forces.

20. A bone screw as defined in claim 1, wherein the first snap-in element is supported on the bone screw so as to be movable in a radial direction.

21. A bone screw as defined in claim 1, wherein the locking elements bear the first snap-in element.

22. A bone screw as defined in claim 1, wherein the head has tab-like wall sections separated by slots extending parallel to the longitudinal axis and wherein the wall sections form the locking elements.

23. A bone screw as defined in claim 1, wherein the locking elements take up the position of engagement in a basic position, no external forces acting on the bone screw in said basic position.

24. A bone screw as defined in claim 1, wherein for the insertion of the securing element into the hole the locking elements are movable radially outwards from the position of engagement.

25. A bone screw as defined in claim 1, wherein the third snap-in element is a snap-in nose acting in a proximal direction and projecting radially outwards and wherein the fourth snap-in element is a snap-in edge projecting radially inwards and acting in a distal direction.

26. A bone screw as defined in claim 1, wherein the third or the fourth snap-in element forms the proximal stop and said elements abut on one another in the securing position.

27. A bone screw as defined in claim 1, wherein a slide-on surface adjoins the third or the fourth snap-in element, the respectively other snap-in element being able to slide on said surface during the insertion of the securing element into the hole.

28. A bone screw as defined in claim 1, wherein the securing element is designed in the shape of a set bolt with a bolt shaft and a bolt head.

29. A bone screw as defined in claim 28, wherein the bolt shaft forms the securing element section designed in the shape of an external polyhedron.

30. A bone screw as defined in claim 28, wherein the bolt head bears the third snap-in element.

31. A bone screw as defined in claim 1, wherein the bone screw has a tool element adapter adapted to be brought into engagement with a screw-in tool for the screwing in of the bone screw.

32. A bone screw as defined in claim 31, wherein the securing element bears the tool adapter.

33. A bone screw as defined in claim 31, wherein the tool adapter is a recess in the shape of a slot, a polyhedron or a star-shaped cavity.

34. A bone screw as defined in claim 1, wherein the head and the shaft are designed in one piece.

35. A bone screw as defined in claim 1, wherein the shaft is provided with an external thread with a self-cutting external thread.

36. A bone screw with a shaft defining a longitudinal axis and a head adapted to be brought into engagement with a bone screw receiving means of a bone plate for the releasable connection of the bone screw to the bone plate, wherein a securing element is provided for securing a connection between the bone screw and the bone plate, wherein the bone screw is adapted to be brought from a position of engagement, the bone screw being held on the bone plate in said position, into a release position, the bone screw being releasable from the bone plate in said release position, wherein the securing element is adapted to be brought from a non-securing position, the bone screw being adapted to be brought into the release position in said non-securing position, into a securing position for securing the connection between the bone screw and the bone plate, the bone screw taking up the position of engagement in said securing position, wherein the securing element is supported on the bone screw so as to be movable, the bone screw further comprising at least one holding element, the at least one holding element exerting a biasing force on the securing element in the direction of the longitudinal axis to hold the securing element in the securing position, the securing element being held in the securing position in a basic position of the bone screw, with no external forces acting on the bone screw in said basic position, said holding element being supported on at least one of the shaft and on the securing element, the holding element being designed in such a manner that an external dimension and/or a volume of the holding element is variable due to alteration to at least one state parameter in the surroundings of the bone screw, the at least one state parameter being ambient temperature, ambient pressure, osmotic pressure or humidity of the surroundings, wherein the holding element is inflatable by means of a fluid.

37. An implant system comprising at least one bone plate with at least one bone screw receiving means and at least one bone screw adapted to be brought into engagement with the bone screw receiving means in a position of engagement for the releasable connection of the bone screw to the bone plate, wherein the bone screw has a shaft defining a longitudinal axis and a head adapted to be brought into engagement with a bone screw receiving means of a bone plate for the releasable connection of the bone screw to the bone plate, wherein a securing element is provided for securing a connection between the bone screw and the bone plate, wherein the bone screw is adapted to be brought from a position of engagement, the bone screw being held on the bone plate in said position, into a release position, the bone screw being releasable from the bone plate in said position, wherein the securing element is adapted to be brought from a non-securing position, the bone screw being adapted to be brought into the release position in said non-securing position, into a securing position for securing the connection between the bone screw and the bone plate, the bone screw taking up the position of engagement in said securing position, wherein the securing element is supported on the bone screw so as to be movable, the bone screw further comprising at least one holding element, the at least one holding element exerting a biasing force on the securing element in the direction of the longitudinal axis to hold the securing element in the securing position, the head bearing a first snap-in element adapted to be interlocked with a second snap-in element arranged on the bone plate in the position of engagement, the shaft having a hole, the securing element being supported in the hole, the head comprising a plurality of locking elements movable transversely to the longitudinal axis, said locking elements being in engagement with the bone plate in the position of engagement, the bone screw further comprising a second snap-in device comprising a third snap-in element and a fourth snap-in element interacting with the third snap-in element, wherein the securing element and the head each bear a snap-in element and wherein the second snap-in device takes up a snap-in position after the insertion of the securing element into the hole, wherein the locking elements bear the fourth snap-in element.

* * * * *